(12) United States Patent
Callegari et al.

(10) Patent No.: US 9,367,710 B2
(45) Date of Patent: Jun. 14, 2016

(54) WATCH IDENTIFICATION AND AUTHENTICATION SYSTEM AND METHOD

(71) Applicant: SICPA HOLDING SA, Prilly (CH)

(72) Inventors: Andrea Callegari, Chavannes-pres-Renens (CH); Lorenzo Sirigu, Lausanne (CH); Christine Reinhard, Prilly (CH); Eric Decoux, Vevey (CH); Thierry Mauron, La Tour-de-Prene (CH); Yves Berthier, Metabief (FR)

(73) Assignee: SICPA HOLDING SA, Prilly (CH)

( * ) Notice: Subject to any disclaimer, the term of this patent is extended or adjusted under 35 U.S.C. 154(b) by 433 days.

(21) Appl. No.: 13/757,296

(22) Filed: Feb. 1, 2013

(65) Prior Publication Data

US 2013/0200143 A1 Aug. 8, 2013

Related U.S. Application Data

(60) Provisional application No. 61/594,734, filed on Feb. 3, 2012.

(30) Foreign Application Priority Data

Feb. 6, 2012 (EP) .................................. 12154063

(51) Int. Cl.
*G06F 17/00* (2006.01)
*G06K 5/04* (2006.01)
(Continued)

(52) U.S. Cl.
CPC ...... *G06K 5/04* (2013.01); *G01N 21/23* (2013.01); *G01N 21/6408* (2013.01); *G01N 21/87* (2013.01); *G04B 47/04* (2013.01); *G04D 7/00* (2013.01); *G06K 7/10821* (2013.01)

(58) Field of Classification Search
CPC ...... G01N 21/255; G01N 21/23; G01N 21/87
See application file for complete search history.

(56) References Cited

U.S. PATENT DOCUMENTS

| 3,989,379 A | 11/1976 | Eickhorst |
| 6,980,283 B1 | 12/2005 | Aggarwal |

(Continued)

FOREIGN PATENT DOCUMENTS

| CH | 694111 A5 | 7/2004 |
| CN | 1224885 A | 8/1999 |

(Continued)

OTHER PUBLICATIONS

Chinese Office Action in counterpart Chinese Application No. 2013800077810, dated Dec. 30, 2015 (with English-language translation).

(Continued)

*Primary Examiner* — Christle I Marshall
*Assistant Examiner* — Asifa Habib
(74) *Attorney, Agent, or Firm* — Greenblum & Bernstein, P.L.C.

(57) ABSTRACT

A method and system for creating and storing an identifier for a timepiece having at least one gemstone. The method includes determining one or more characteristics of the at least one gemstone and detecting a relative position of the at least one gemstone in the timepiece. The method further includes creating the identifier for the timepiece in dependence upon at least one of the one or more characteristics of the at least one gemstone and the respective relative position of the at least one gemstone and storing the identifier in a database or device.

2 Claims, 12 Drawing Sheets

(51) Int. Cl.
*G04B 47/04* (2006.01)
*G06K 7/10* (2006.01)
*G01N 21/23* (2006.01)
*G01N 21/64* (2006.01)
*G01N 21/87* (2006.01)
*G04D 7/00* (2006.01)

(56) References Cited

U.S. PATENT DOCUMENTS

2003/0063772 A1* 4/2003 Smith .................... G07D 7/004
                                                    382/100
2004/0213088 A1* 10/2004 Fuwausa ................ B60K 37/02
                                                    368/228

FOREIGN PATENT DOCUMENTS

| | | |
|---|---|---|
| CN | 2893828 Y | 4/2007 |
| DE | 4406768 A1 | 9/1995 |
| EP | 0072350 | 2/1983 |
| JP | H06306315 A | 11/1994 |
| WO | WO9921061 A1 | 4/1999 |
| WO | WO2011/101724 | 8/2011 |

OTHER PUBLICATIONS

International Search Report in counterpart International Application No. PCT/EP2013/052027 dated May 15, 2013.

* cited by examiner

ΔT= 1.5 ms

ΔT= 1.8 ms

WATCH IDENTIFICATION AND AUTHENTICATION SYSTEM AND METHOD

CROSS REFERENCE TO RELATED APPLICATIONS

The present application claims priority to U.S. Provisional Application No. 61/594,734 filed on Feb. 3, 2012, and to European Patent Application No. 12154063.7 filed on Feb. 6, 2012, the disclosures of which are expressly incorporated by reference herein in their entireties.

FIELD OF THE INVENTION

Embodiments of the present invention relate to timepieces and watches, and more particularly to a watch identification and authentication system and method.

DESCRIPTION OF THE RELATED ART

Counterfeit consumer goods, commonly called knock-offs, are counterfeit or imitation products offered for sale. The spread of counterfeit goods has become global in recent years and the range of goods subject to infringement has increased significantly.

Expensive watches (and spare parts for watches) are vulnerable to counterfeiting, and have been counterfeited for decades. A counterfeit watch is an illegal copy of a part or all of an authentic watch. According to estimates by the Swiss Customs Service, there are some 30 to 40 million counterfeit watches put into circulation each year. It is a common cliché that any visitor to New York City will be approached on a street corner by a vendor with a dozen such counterfeit watches inside his coat, offered at bargain prices. Extremely authentic looking, but very poor quality watch fakes with self-winding mechanisms and fully working movements can sell for as little as twenty dollars. The problem is becoming more and more serious, with the quality of the counterfeits constantly increasing. For example, some fakes' movements and materials are of remarkably passable quality and may look good to the untrained eye and work well for some years, a possible consequence of increasing competition within the counterfeiting community. Counterfeits watches cause an estimated $1 Billion loss per year to the watch industry.

Authentication solutions that have been used for protection of consumer goods from counterfeiting are often based on marking the item with a specific material, code, or marking, engraving, etc. However, these methods modify the nature and the appearance of the object, and this is often not acceptable in the watch (and other luxury items) industry, where the design of the object and its visual appearance is of paramount importance. Also, these methods require an active intervention at the time of manufacturing and, correspondingly an important change of the production process. Another method for identification and/or authentication involves tagging (e.g., a micro tag or RFID tag). The tagging approach, however, requires intervention and may be impracticable. Moreover, such an approach may not fulfill all of watchmakers needs and constraints to protect against counterfeits. Stability and durability of the marking or tag is also a problem, since the lifetime of a timepiece is often measured in tens of years.

Therefore, there is a need for an improved watch identification and authentication system and method that provides the identification/authentication functionalities, while requiring minimal or no intervention in the manufacturing process and/or without any overt marking.

SUMMARY OF THE INVENTION

The present invention provides a method for creating and storing an identifier for a timepiece having at least one gemstone. The method comprises determining one or more characteristics of the at least one gemstone; detecting a relative position of the at least one gemstone in the timepiece; creating the identifier for the timepiece in dependence upon at least one of the one or more characteristics of the at least one gemstone and the respective relative position of the at least one gemstone; and storing the identifier in a database or device.

In further embodiments, the present invention provides a method for authentication and/or identification of a timepiece. The method comprises determining one or more characteristics of the at least one gemstone and detecting a relative position of the at least one gemstone in the timepiece. Additionally, the method comprises creating an obtained identifier for the timepiece in dependence upon at least one of the one or more characteristics of the at least one gemstone and the respective relative position of the at least one gemstone, and comparing the obtained identifier with one or more stored identifiers to determine whether the timepiece is authentic or a counterfeit.

In additional embodiments, the identifier is a unique identifier and may comprise an identifying code.

With embodiments of the invention, the one or more characteristics comprise luminescent properties and/or orientation.

In further embodiments, the determining one or more characteristics comprises determining the one or more characteristics at one or more intervals, which may include determining spectral characteristics at one or more spectral intervals, or determining luminescence at two or more time intervals during which the luminescence is measured.

With embodiments of the invention, the two or more time intervals may be one of simultaneous and sequential, may be overlapping time intervals or non-overlapping time intervals, may be of a same duration or a different duration, may be regularly spaced or irregularly-spaced, and at least one of the two or more time intervals may be different time intervals. In some embodiments, the determining the one or more characteristics comprises determining at least one of spectral characteristics of a luminescence and decay time of the luminescence, wherein the spectral characteristics comprise at least one of intensity and wavelength range of the luminescence. In embodiments of the present invention, the luminescent properties comprise at least one of phosphorescence and fluorescence emitted by the at least one gemstone upon excitation with light.

In further embodiments, the method additionally includes measuring birefringence properties of the at least one gemstone to determine the orientation of the at least one gemstone, which may comprise using one of: polarized light and a polarizing filter, and a plurality of polarizing filters, to measure the birefringence properties of the at least one gemstone. With additional embodiments, the orientation of a respective gemstone is identified based on an orientation of one or more of the optical axes of the respective gemstone.

With embodiments of the invention, the timepiece comprises one of a watch and a clock.

In some embodiments, the creating the identifier comprises converting the detected relative position of the at least one gemstone and corresponding determined characteristics of the at least one gemstone into a digital representation.

With additional embodiments, the at least one gemstone comprises corundum. Additionally, in some embodiments, the corundum further comprises one or more dopant metal ions in the $4^{th}$ period of the periodic table of the elements present up to a few percent concentration. In embodiments, the dopant concentration includes a range of 0.1% to 5%. In particular embodiments, the dopant metal ions comprises $Cr3+$. In further embodiments, the at least one gemstone comprises garnet, wherein in embodiments, the garnet comprises one or more dopant metal ions from the rare earth metals, which may comprise one or more dopant metal ions from the group consisting of: Nd, Er, Yb, Tm, and Ho. Additionally, in embodiments, the gemstone may be natural or synthetic According to aspects of the invention, in embodiments, the detecting the relative position of a respective gemstone comprises determining coordinates (a1, b1) of the respective gemstone with respect to a coordinate system associated with the timepiece.

In some embodiments, the one or more stored identifiers are stored in a database.

Additional embodiments of the invention are directed to a method for creating and storing an identifier from a timepiece having at least one gemstone. The method comprises measuring characteristics including at least one of: (1) luminescent properties of the at least one gemstone; (2) a relative position of the at least one gemstone in the timepiece; and (3) birefringence properties of the at least one gemstone, creating the identifier for the timepiece in dependence upon the measured characteristics; and storing the identifier in a database or device.

Further embodiments of the invention are directed to a method for authentication and/or identification of a timepiece having at least one gemstone. The method comprises measuring characteristics including at least one of: (1) luminescent properties of the at least one gemstone; (2) a relative position of the at least one gemstone in the timepiece; and (3) birefringence properties of the at least one gemstone. The method additionally includes creating an obtained identifier for the timepiece in dependence upon the measured characteristics; and comparing the obtained identifier with one or more stored identifiers to determine whether the timepiece is authentic or a counterfeit.

Additional embodiments of the invention provide a system for determining an identifier from a timepiece having at least one gemstone. The system comprises at least one reader configured to determine one or more characteristics of the at least one gemstone in the timepiece, including at least one of: (1) luminescent properties of the at least one gemstone; (2) a relative position of the at least one gemstone in the timepiece; and (3) birefringence properties of the at least one gemstone. The system additionally comprises a processor for creating the identifier for the timepiece in dependence upon at least one of the one or more characteristics of the at least one gemstone and the respective relative position of the at least one gemstone, and a storage system configured for storing the identifier.

With further embodiments, the system additionally comprises a comparator configured for comparing the identifier to one or more stored identifiers in order to identify the timepiece as one of authentic and a counterfeit.

Additional embodiments of the invention are directed to a timepiece comprising a movement having at least one gemstone selected to create an identifier for the timepiece based on one or more characteristics of the at least one gemstone. In some embodiments, the identifier comprises one or more predetermined elements, and the at least one gemstone is selected to indicate the one or more predetermined elements upon detection of the one or more characteristics.

Additional embodiments of the invention are directed to a timepiece comprising a movement having at least one gemstone, in combination with a storage system configured for storing an identification number of the timepiece in association with an identifier of the timepiece, wherein the identifier corresponds to gemstone characteristics of one or more gemstones of the timepiece.

Further embodiments of the present invention are directed to a method of making a timepiece having at least one gemstone. The method comprises installing at least one gemstone selected to create an identifier for the timepiece based on one or more characteristics of the at least one gemstone. In embodiments, the identifier comprises one or more predetermined elements, and the at least one gemstone is selected or oriented to indicate the one or more predetermined elements upon detection of the one or more characteristics.

According to additional aspects of the invention, in embodiments, a database is configured for storing a plurality of timepiece identifier. The database comprises a storage system configured for storing an identification number of a timepiece in association with an identifier of the timepiece. In embodiments, the identifier corresponds to gemstone characteristics of one or more gemstones of the timepiece. In embodiments, the identifier comprises a numerical or alpha-numerical representation of the gemstone characteristics of the one or more gemstones of the timepiece.

In further embodiments, the method also includes issuing a signal indicating one of authenticity of the timepiece and non-authenticity of the timepiece.

In additional embodiments, the signal comprises at least one of: an alert, a hold signal, an alarm, and a notification.

BRIEF DESCRIPTION OF THE DRAWINGS

For a more complete understanding of the invention, as well as other objects and further features thereof, reference may be had to the following detailed description of the invention in conjunction with the following exemplary and non-limiting drawings wherein.

Figure 1:
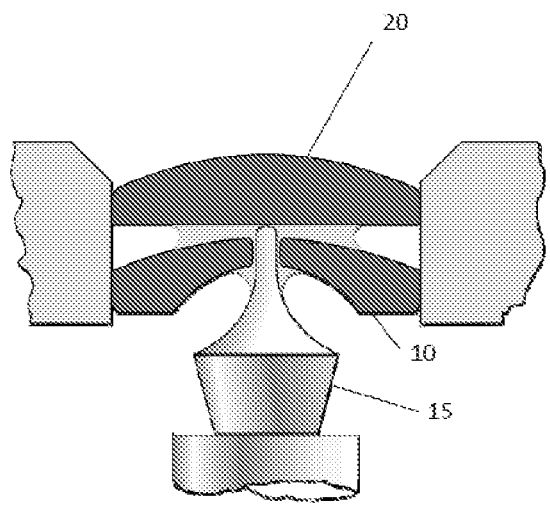
FIG. 1 illustrates an exemplary cross section view of components of a watch.

Reference numbers refer to the same or equivalent parts of the present invention throughout the various figures of the drawings.

DETAILED DESCRIPTION OF THE INVENTION

In the following description, the various embodiments of the present invention will be described with respect to the enclosed drawings.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

As used herein, the singular forms "a," "an," and "the" include the plural reference unless the context clearly dictates otherwise. For example, reference to "a magnetic material" would also mean that mixtures of one or more magnetic materials can be present unless specifically excluded.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The various embodiments disclosed herein can be used separately and in various combinations unless specifically stated to the contrary.

A watch is a small timepiece, typically worn either on the wrist or attached on a chain and carried in a pocket, with wristwatches being the most common type of watch used today. A mechanical watch is a watch that uses a mechanical mechanism to measure the passage of time, as opposed to modern quartz watches which function electronically.

The internal mechanism of a watch, excluding the face and hands, is called the movement. The watch is driven by a spring (called a mainspring), which is wound periodically to store mechanical energy to power the watch. The mainspring's force is transmitted through a series of gears (or gear train) to power the balance wheel. The gear train has the dual function of transmitting the force of the mainspring to the balance wheel and adding up the swings of the balance wheel to get units of seconds, minutes, and hours, etc. A separate part of the gear train, called the keyless work, allows the user to wind the mainspring and enables the hands to be moved to set the time.

The balance wheel is a weighted wheel that oscillates back and forth at a constant rate. Each swing of the balance wheel takes precisely the same amount of time. This is the timekeeping element in the watch. An escapement mechanism has the dual function of keeping the balance wheel vibrating by giving it a push with each swing, and allowing the clock's gears to advance or 'escape' by a set amount with each swing, moving the watch's hands forward at a constant rate. The periodic stopping of the gear train by the escapement makes the 'ticking' sound of the mechanical watch. An indicating dial, usually a traditional clock face with rotating hands, is used to display the time in human-readable form.

Jewel bearings were introduced in watches to reduce friction. The advantage of using jewels is that their ultrahard slick surface has a lower coefficient of friction with metal. Jewels in modern watches are usually synthetic sapphire or (usually) ruby, made of corundum ($Al_2O_3$), one of the hardest substances known (only diamond is harder). Corundum is clear in color. The only difference between sapphire and ruby is that different impurities have been added to change the clear color of the corundum; there is no difference in their properties as a bearing.

Jewels serve multiple purposes in a watch. First, reduced friction can increase accuracy. Friction in the wheel train bearings and the escapement causes slight variations in the impulses applied to the balance wheel, causing variations in the rate of timekeeping. The low, predictable friction of jewel surfaces reduces these variations. Second, the jewels can increase the life of the bearings.

Watches utilize two different types of jewels in bearings. Hole jewels are donut shaped sleeve bearings used to support the arbor (or shaft) of most wheels. Capstones (or cap jewels) are positioned at each end of the arbor. When the arbor is in a vertical position, its rounded end bears against the surface of the capstone, lowering friction.

FIG. 1 illustrates an exemplary cross section view of components of a watch. As shown in FIG. 1, a hole jewel 10 is used to support the arbor (or shaft) 15, and a capstone (or cap jewel) 20 is positioned at each end of the arbor (with only one end shown in FIG. 1).

Jewels are also utilized in the escapement for the parts that function by sliding friction. For example, pallets are the angled rectangular surfaces on the lever that are pushed against by the teeth of the escape wheel. The pallets are a primary source of friction in a watch movement, and were one of the first sites to which jewels were applied.

The number of jewels used in watch movements increased over the last 150 years as jeweling grew less expensive and watches grew more accurate. The only bearings that really need to be jeweled in a watch are the ones in the going train—the gear train that transmits force from the mainspring barrel to the balance wheel—since only they are constantly under force from the mainspring. The wheels that turn the hands (the motion work) and the calendar wheels are not under load, while the ones that wind the mainspring (the keyless work) are used very seldom, so they do not wear significantly. Friction has the greatest effect in the wheels that move the fastest, so they benefit most from jeweling. So the first mechanism to be jeweled in watches was the balance wheel pivots, followed by the escapement. As more jeweled bearings were added, they were applied to slower moving wheels, and jeweling progressed up the going train toward the barrel. A seventeen jewel watch has every bearing from the balance wheel to the center wheel pivot bearings jeweled, so it was considered a 'fully jeweled' watch. In quality watches, to minimize positional error, capstones were added to the lever and escape wheel bearings, making twenty-one jewels. Even the mainspring barrel arbor was sometimes jeweled, making the total twenty-three. When self winding watches were introduced in the 1950s, several wheels in the automatic winding mechanism were jeweled, increasing the count to twenty-five-twenty-seven.

In accordance with aspects of the invention, one or more properties of a plurality of the jewels (or gemstones) are used for identification and/or authentication of a timepiece. It has been surprisingly found that the jewels can be used for authentication and/or identification, by analysis of specific characteristics, linked to the nature of the jewel, its chemical composition and/or its physical properties. In embodiments, these characteristics for a respective jewel include the luminescence of the stone, its position in space, and its orientation.

By implementing aspects of the invention, a watch can be uniquely identified through an analysis and measurement of the specific characteristics of one or more jewels of the watch. The analysis and measurement may be performed, for example, during or after manufacture of the watch. In embodiments, these specific characteristics of the jewels (or, for example, a numerical representation thereof) can be stored in a storage system (e.g., a database) along with an identification number (e.g., a serial number). Subsequently, by performing the analysis and measurement of the specific characteristics of one or more jewels, and comparing the measured results with results previously stored in the storage system, the watch can be authenticated. If the measured results match a previously stored identification (or the previously stored identification associated with the identification number of the watch), then the watch is deemed authentic.

While a watch may have, for example, as many as twenty-seven jewels, typically five to seven jewels (and sometime more) are visible in the movement, for example, through a clear back plate, or after the back plate has been removed. In embodiments, the invention contemplates that the five to seven viewable jewels may be used for identification and/or authentication. The invention contemplates, however, that in embodiments, jewels other than the "visible" jewels (which are viewable, for example, after further disassembly of the timepiece, or prior to complete assembly of the timepiece) may be used, for example, as an alternative to, or in addition to, the "visible" jewels, for identification and/or authentication.

Embodiments of the present invention provide an improved watch identification and authentication system and method that provides the identification and authentication functionalities, while requiring minimal or no intervention in the manufacturing process.

Jewel Luminescence

Natural and synthetic ruby is mainly composed of $Cr:Al_2O_3$, and it is used in watches for its mechanical properties, and sometimes, for its color. Natural and synthetic ruby also has other interesting properties. For example, rubies, due to the Cr doping, exhibit intense and long lived luminescence ($\lambda \sim 700$ nm, $\tau \sim 3.5$ ms), wherein $\lambda$ is the wavelength of luminescence, and $\tau$ is the lifetime of the luminescence. Due to the strength of the luminescence, this characteristic is easily measurable. In accordance with aspects of the invention, ruby luminescence is utilized as a security feature. $\tau$ depends, for example, on the concentration of Cr and other impurities. While the above example utilizes chromium doping, the invention contemplates that, in embodiments, other (or additional) types of dopants may be used, which may result in the jewels exhibiting differing lifetimes and/or luminescence ranges. For example, Ti or Fe doping (amongst other contemplated dopants) may be used to modulate the luminescence lifetime. Other types of contemplated dopants, in particular, with garnets (which are slightly less hard than corundum, but are also used in timepieces), include rare earths, such as, Nd, Er, Yb, Tm, and Ho. In accordance an exemplary aspect of the invention, the natural variations of the stones (e.g., commercial stones) can be exploited to create an identification and authentication security feature. Additionally, in embodiments of the present invention, a manufacturer may use jewels that were synthesized to have a target synthesis (e.g., particular properties). For example, the concentration of dopants can be specified at the synthesis. While rubies are noted above, in embodiments, the stones may be corundum ($Al_2O_3$) and/or garnet containing one or more "dopant" metal ions in the $4^{th}$ period (Fe, Ti, V, Cr, . . . ) present, for example, up to a few percent concentration. For example, in embodiments, the few percent concentration includes a range of 0.1% to 5%. In embodiments, the dopant ions may be Cr3+. In embodiments, the jewels can be natural and/or synthetic.

According to embodiments of the invention, a watch is subject to an illumination source, and the luminescence of a number of jewels of the watch are measured over a period of intervals. By luminescence, it is intended phosphorescence and/or fluorescence emitted by a stone upon excitation with light. In embodiments, the intervals may be time intervals (e.g., 1 to 10 ms) for measuring luminescence, or may be spectral intervals (e.g., $\lambda=690$-710 nm).

Figure 2:
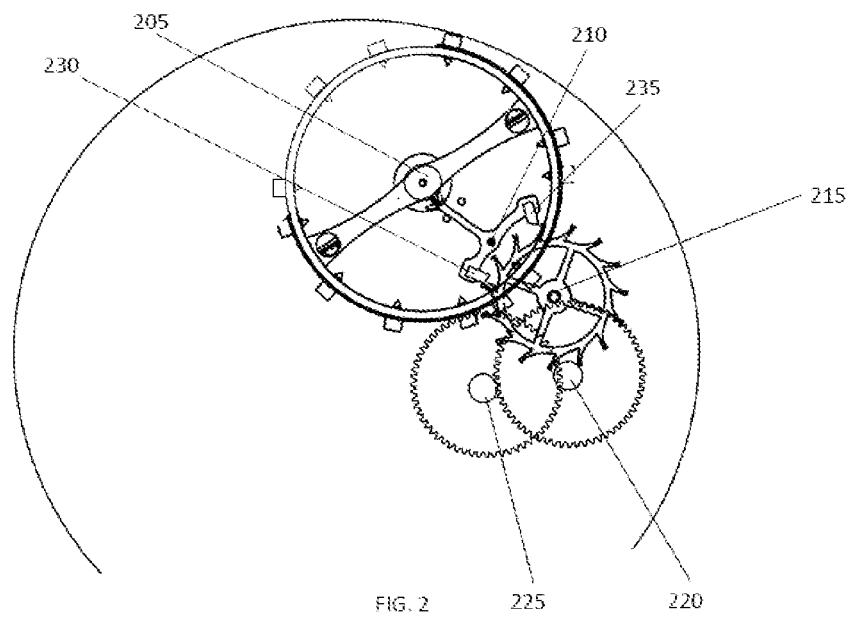
FIG. 2 illustrates an exemplary schematic view of a watch showing jewels subject to illumination in accordance with aspects of the present invention.

FIG. 2 illustrates an exemplary schematic view of a watch showing jewels that are subjected to illumination. As should be understood, FIG. 2 represents a schematic illustration of a watch, and does not illustrate all the components of the watch. As shown in FIG. 2, with this exemplary and non-limiting embodiment, seven jewels (205, 210, 215, 220, 225, 230, and 235) have been subjected to illumination. As should be understood, different watches may have differing numbers of jewels and/or differing number of viewable jewels (e.g., through a transparent back and/or upon removal of a back cover), and the invention contemplates using any number of jewels for identification and/or authentication. As shown in FIG. 2, jewels 205, 210, 215, 220, and 225 are capstone jewels, whereas jewels 230 and 235 are escapement jewels.

Figure 3:
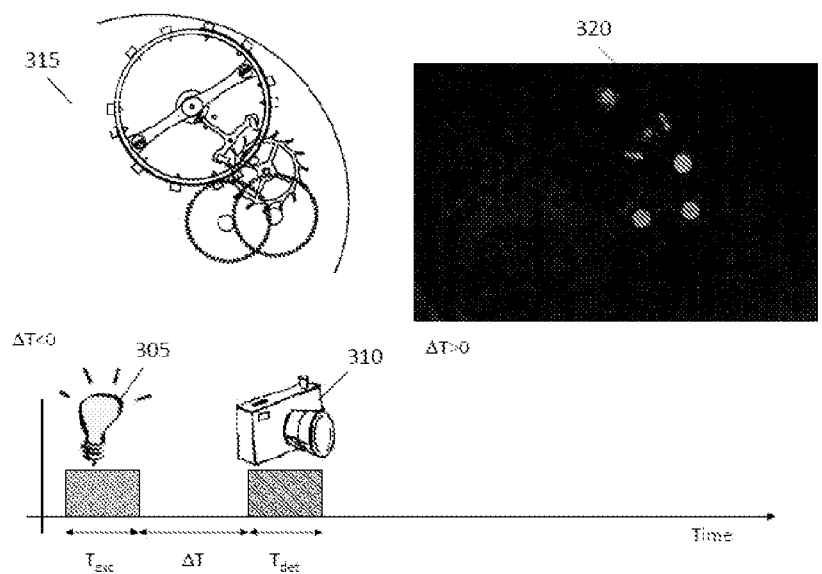
FIG. 3 illustrates an overview of the jewel luminescence measurement in accordance with aspects of the invention.
Figure 4:
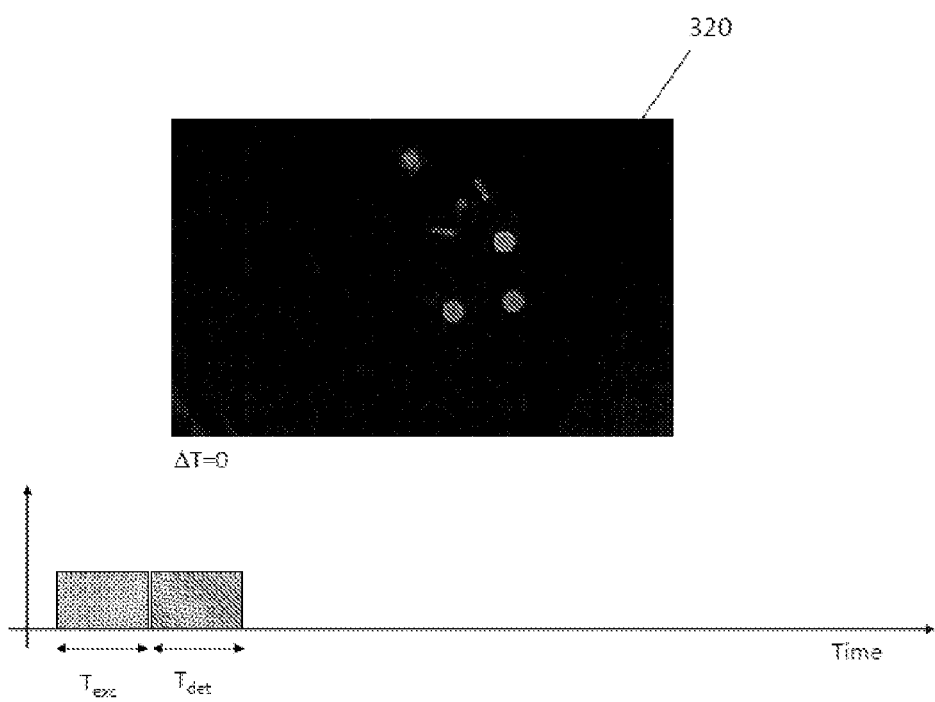
FIGS. 4-15 illustrate detection and measurements of the luminescence of the jewels.
Figure 5:
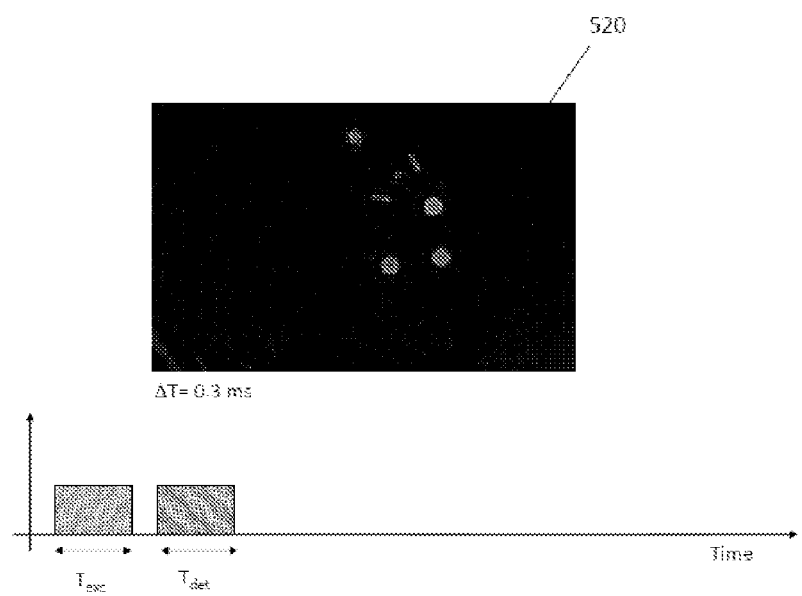
Figure 6:
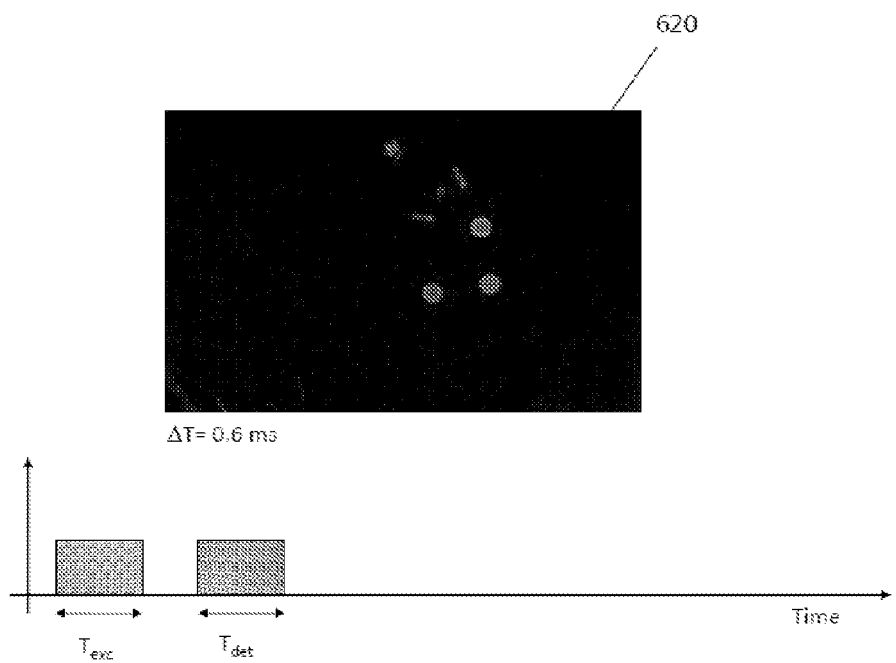
Figure 7:
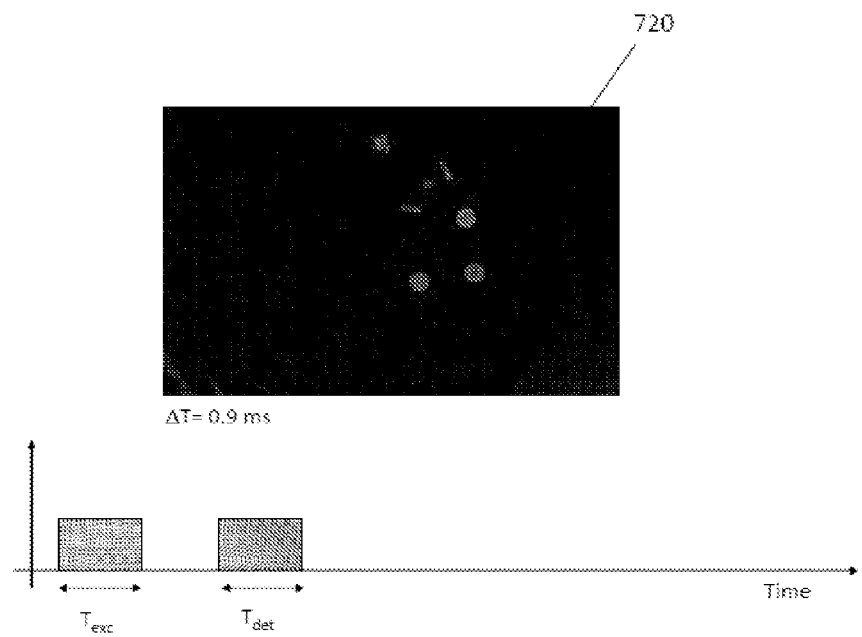
Figure 8:
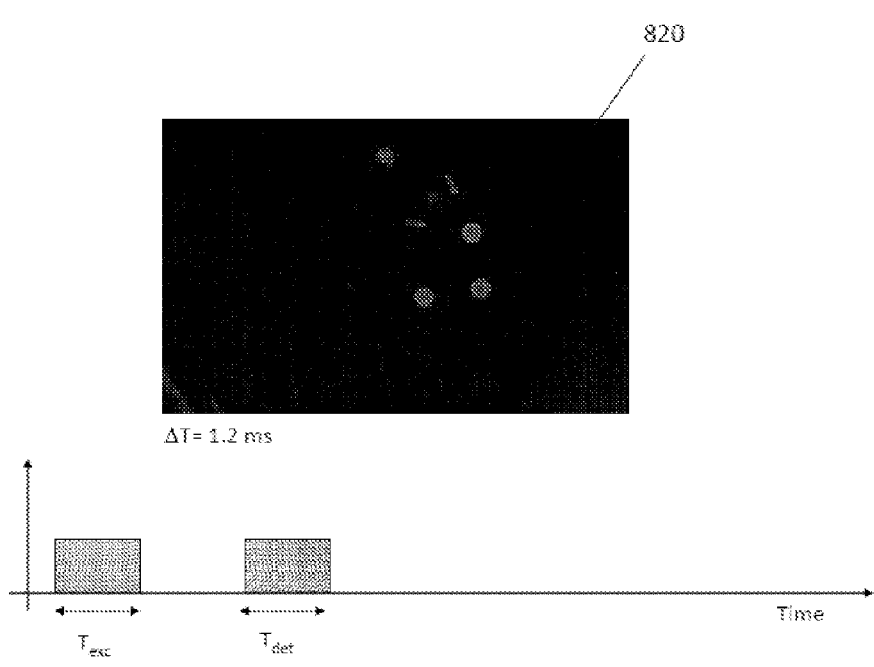
Figure 9:
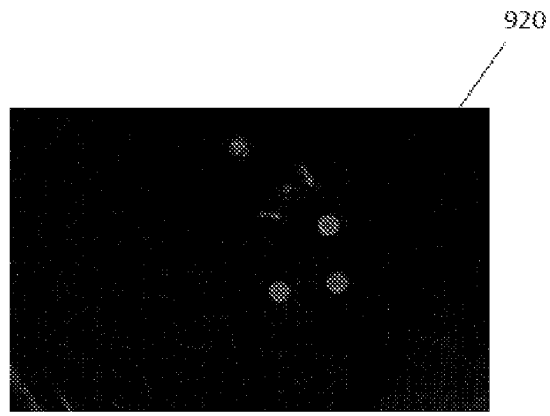
Figure 9:
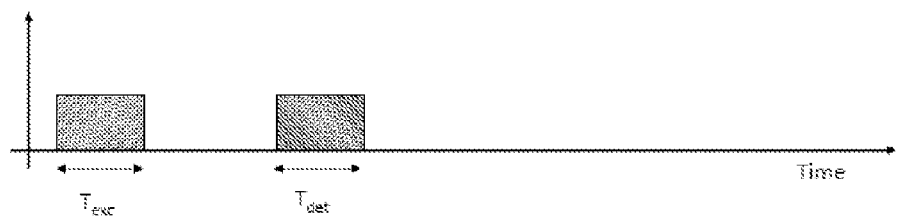
Figure 10:
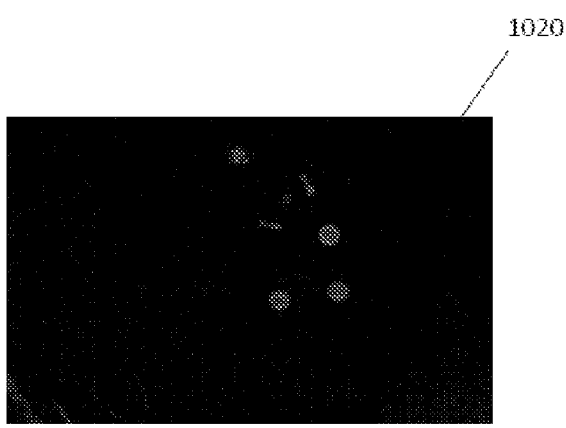
Figure 10:
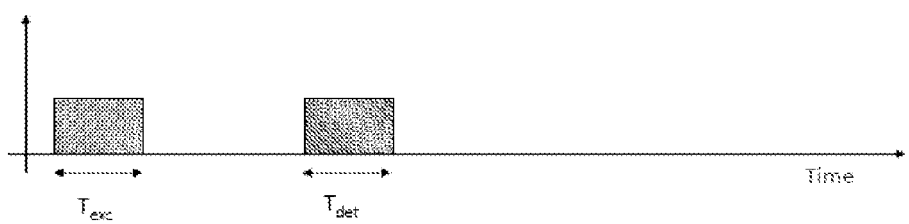
Figure 11:
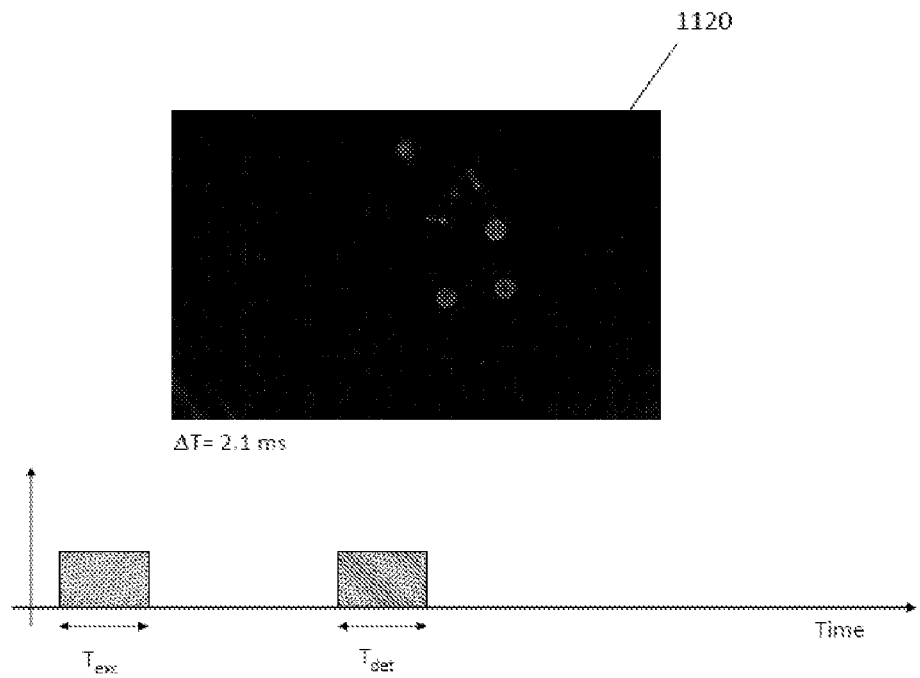
Figure 12:
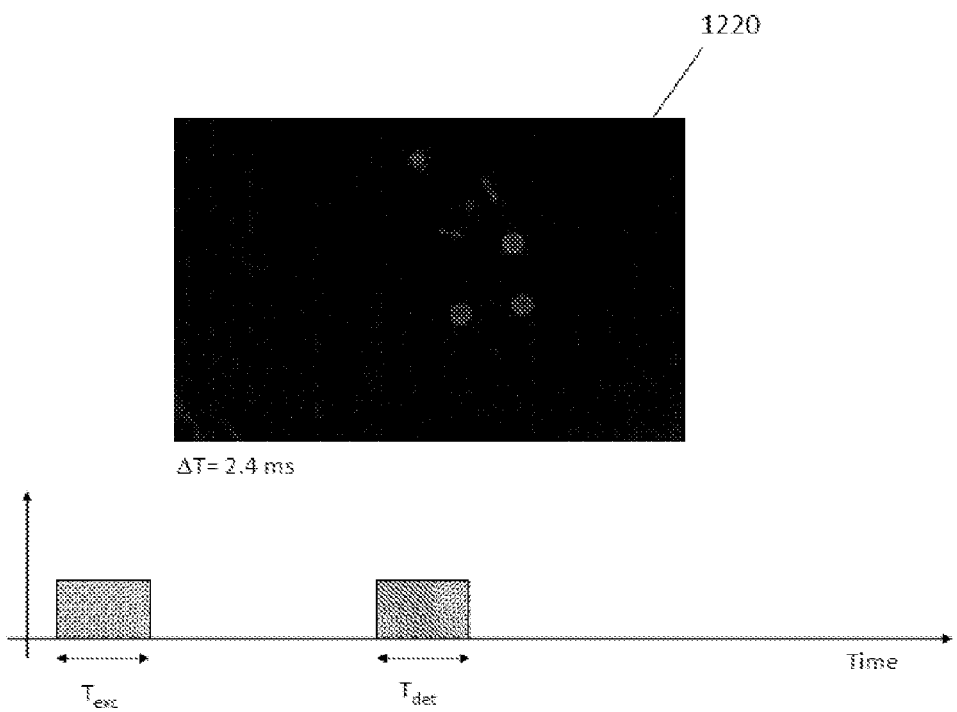
Figure 13:
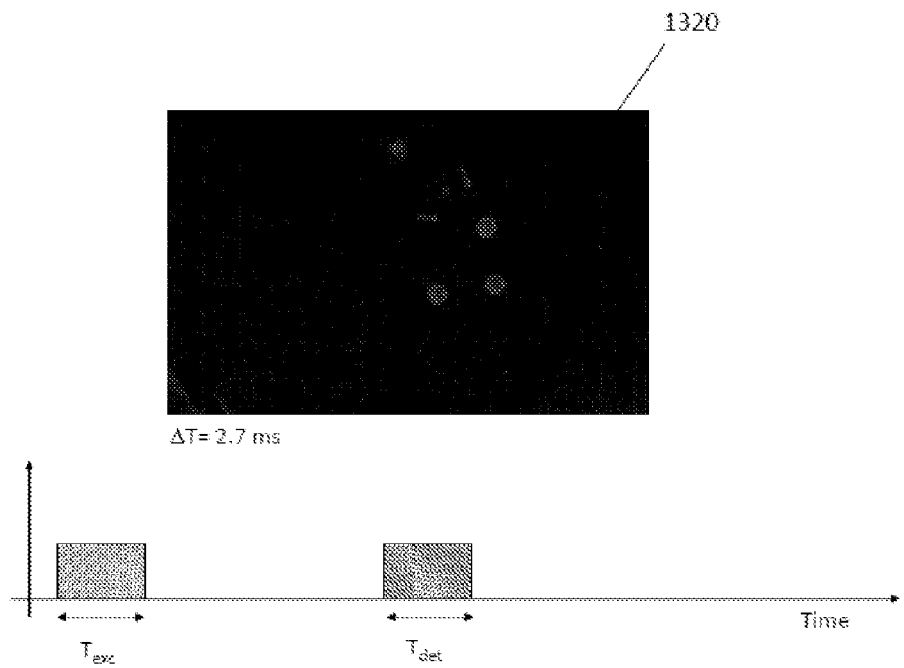
Figure 14:
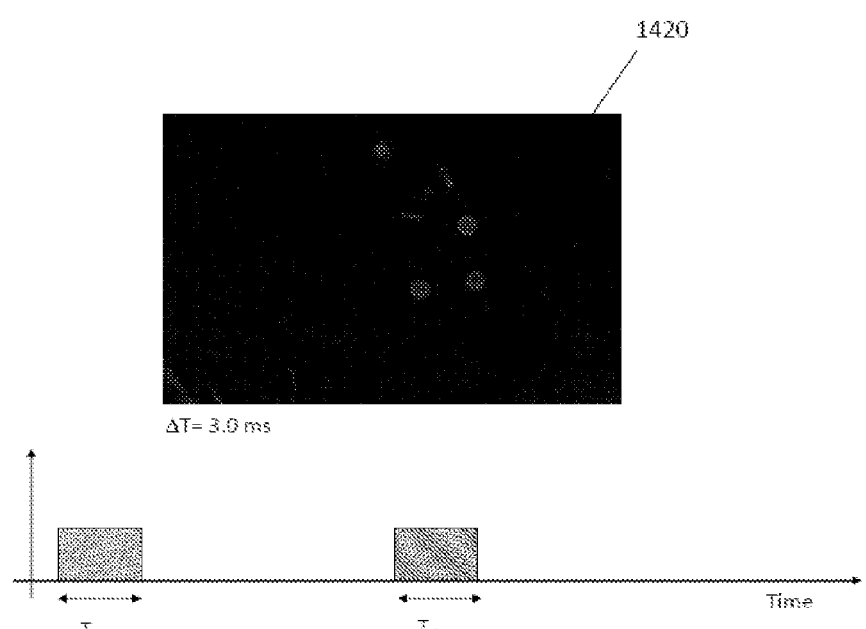

FIG. 3 illustrates an overview of the jewel luminescence measurement in accordance with aspects of the invention. As shown in FIG. 3, during the time period $T_{exec}$, an illumination source 305 is activated to provide excitation light to the jewels of a watch. After an elapse of time, $\Delta T$, the luminescence of the jewels is detected and measured by a reader 310 during $T_{det}$. Image 315 schematically illustrates the jewels during illumination with the excitation light. Image 320 illustrates the jewels during the time period $T_{det}$. In embodiments, the reader 310 may comprise, for example, a fixed device, a handheld device, a mobile phone, and/or a camera, amongst other contemplated readers.

In accordance with aspects of the invention, the luminescence of the jewels may be detected and measured at several intervals. By several intervals, it is intended two or more time intervals, which can be the same or different (e.g., a plurality of jewels' luminescence are measured during the same time interval, i.e., simultaneously, or, during different time intervals, i.e., sequentially), overlapping or non-overlapping, have the same duration or different duration, be regularly spaced or not, during which the luminescence is measured.

Figure 15:
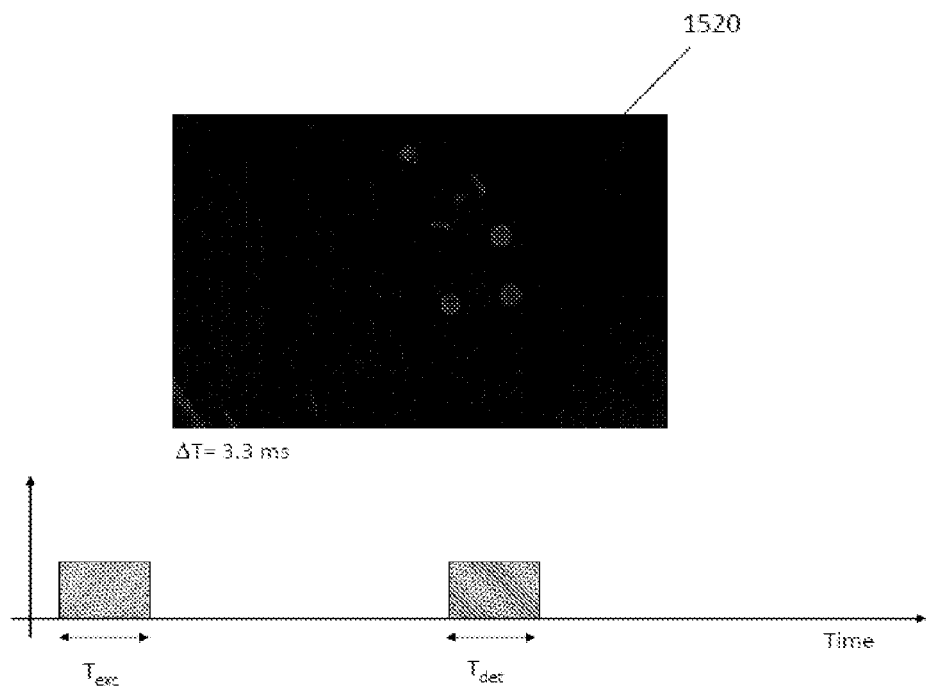

FIGS. 4-15 illustrate an exemplary and non-limiting detection and measurement of the luminescence of the jewels at different intervals of 0.3 ms in duration from $\Delta T=0$ (FIG. 4) to $\Delta T=3.3$ ms (FIG. 15). Additionally, FIGS. 4-15 also show respective images (420, 520, 620, 720, 820, 920, 1020, 1120, 1220, 1320, 1420, and 1520) of the detected luminescence during $T_{det}$. In embodiments, measuring the luminescence includes determining spectral characteristics (intensity and/or wavelength) of the luminescence, and/or determining a lifetime (also called decay time) of the luminescence.

Figure 16:
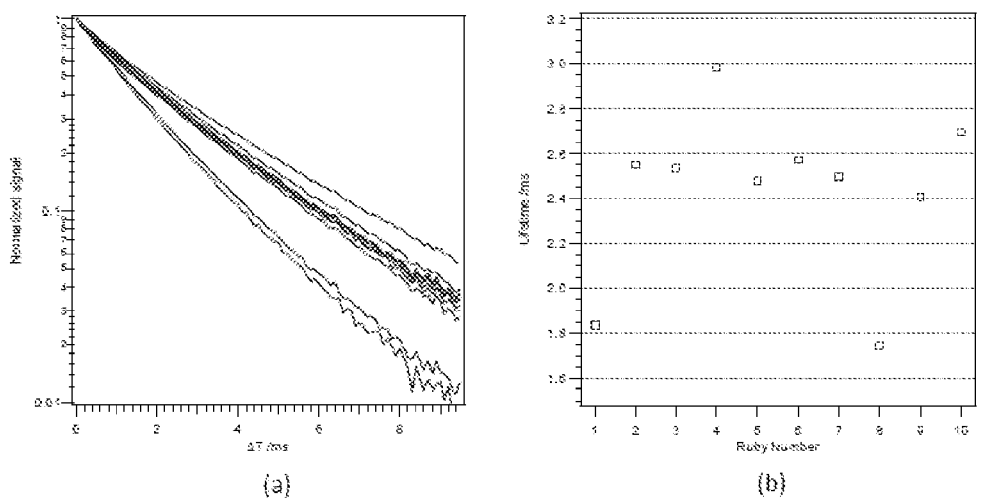
FIG. 16 illustrates exemplary camera measurement results in accordance with aspects of the invention.

FIG. 16 illustrates exemplary camera measurement results on ten rubies from the same supplier in accordance with aspects of the invention. FIG. 16(*a*) illustrates decay curves for the ten rubies (with each ruby represented by a plotted line). FIG. 16(*b*) illustrates respective lifetimes for the ten rubies. As shown in FIG. 16(a), the ten different rubies exhibit different decay curves. As shown in FIG. 16(b), the ten different rubies exhibit different lifetimes. Moreover, as shown in FIG. 16(b), with this exemplary batch of ten rubies (labeled ruby number 1 through ruby number 10), ruby numbers 1, 4, 8, and 10 are relative outliers. This illustrates the variability in decay rates amongst the different jewels (even, for example, within a same batch from the same supplier), and thus, the suitability of detected luminescence for identification and authentication purposes.

Jewel Position

In accordance with additional aspects of the invention, the relative positions of the respective jewels may be detected, e.g., by the reader. In embodiments, the position may comprise the coordinates (x1, y1) of a stone with respect to a coordinate system associated with the timepiece. In further embodiments, the jewels may be identified by a position number (e.g., "Position 1," "Position 2," etc.). Additionally, the relative position of each jewel may be associated (for example, in a database) with the respective luminescent properties (e.g., lifetime, decay curve, decay rate, etc.) for identification and/or authentication. Thus, with reference to FIG. 2, in embodiments, the respective luminescent properties of each of the seven jewels (205, 210, 215, 220, 225, 230, and 235) are detected and associated (e.g., in a database) with the relative positions of the respective jewels. For example, $\tau_0 = 1.1$ ms, $\tau_1 = 1.5$ ms, $\tau_2 = 1.5$ ms, $\tau_3 = \ldots$, $\tau_4 = \ldots$, $\tau_5 = \ldots$, $\tau_6 = \ldots$, wherein $\tau$ is the lifetime, and 0-6 is the jewel number (or relative jewel position). In accordance with aspects of the invention, this association between the luminescent properties and relative locations of the respective jewels creates a map, for example, of which jewel has which lifetime, and provides a unique (or substantially unique) identifier or biometric signature for the watch for identification and/or authentication. As should be understood, the invention contemplates that any number of jewels may serve as an identifier or biometric signature, with a larger number of jewels providing a greater level of uniqueness.

Jewel Orientation

Within a timepiece, the jewels (e.g., the capstones) are round, and when assembled, are positioned arbitrarily with respect to a rotation axis. That is, while two watches of a same manufacturer may have the same layout of jewels (i.e., corresponding jewels are placed in the same relative location, these jewels are arbitrarily placed with respect to an orientation about the jewels' axes, such that the two watches will have the jewels positioned at differing orientations. Thus, in accordance with additional aspects of the invention, the orientation of one or more jewels may be used as an identifier for identification and/or authentication of a timepiece. The orientation of the stones can be measured in a simple way when the stones are made of a birefringent material, such as, for example, corundum, as explained further below.

In accordance with additional aspects of the invention, the relative orientation of the respective jewels may be detected, e.g., by the reader. Additionally, the relative orientation of each jewel may be associated (for example, in a database) with the respective position of each jewel and/or the respective luminescent properties (e.g., lifetime, decay rate, etc.) for identification and/or authentication.

In addition to the luminescent properties noted above, natural or synthetic rubies and corundum, for example, also have other interesting properties. For example, rubies and corundum exhibit strong birefringence. Birefringence, or double refraction, is the decomposition of a ray of light into two rays when it passes through certain anisotropic materials, such as crystals of calcite or boron nitride, and the property of such materials. The simplest instance of the effect arises in materials with uniaxial anisotropy. That is, the structure of the material is such that it has an axis of symmetry with no equivalent axis in the plane perpendicular to it. This axis is known as the optical axis of the material, and light with linear polarizations parallel and perpendicular to it experiences unequal indices of refraction, denoted $n_e$ and $n_o$, respectively, where the suffixes stand for extraordinary and ordinary. The names reflect the fact that, if unpolarized light enters the material at a nonzero acute angle to the optical axis, the component with polarization perpendicular to this axis will be refracted as per the standard law of refraction, while the complementary polarization component will refract at a nonstandard angle determined by the angle of entry and the difference between the indices of refraction, $\Delta n = n_e - n_o$, known as the birefringence magnitude. The light will therefore split into two linearly polarized beams, known as ordinary and extraordinary.

For a given propagation direction, in general there are two perpendicular polarizations for which the medium behaves as if it had a single effective refractive index. In a uniaxial material, rays with these polarizations are called the extraordinary and the ordinary ray (e and o rays), corresponding to the extraordinary and ordinary refractive indices. In a biaxial material, there are three refractive indices $\alpha$, $\beta$, and $\gamma$, yet only two rays, which are called the fast and the slow ray. The slow ray is the ray that corresponds to the highest effective refractive index.

Thus, in accordance with aspects of the invention, ruby birefringence may be utilized as a security feature. The ruby birefringence is approximately: $n_\omega = 1.768$-$1.770$, $n_\epsilon = 1.760$-$1.763$, $\Delta n \sim 0.008$, wherein the direction of optical axes depends on the stone orientation. In accordance with aspects of the invention, stone orientation may easily be measured with an optical method (for example, polarized light with a polarized filter, or crossed polarizers) to determine the relative orientation of one or more of the optical axes of a birefringent stone. A particularly simple method involves using two crossed linear polarizers, one for polarizing the light used to illuminate the stone and the other one to analyze the light reflected by the stone. The relative orientation of the two polarizers with respect to the stone is then changed, either by turning the polarizers or by turning the stone, until a minimum of the reflected intensity is observed. At this position the axis of the polarizers are aligned with the fast and slow directions described above.

Figure 17:
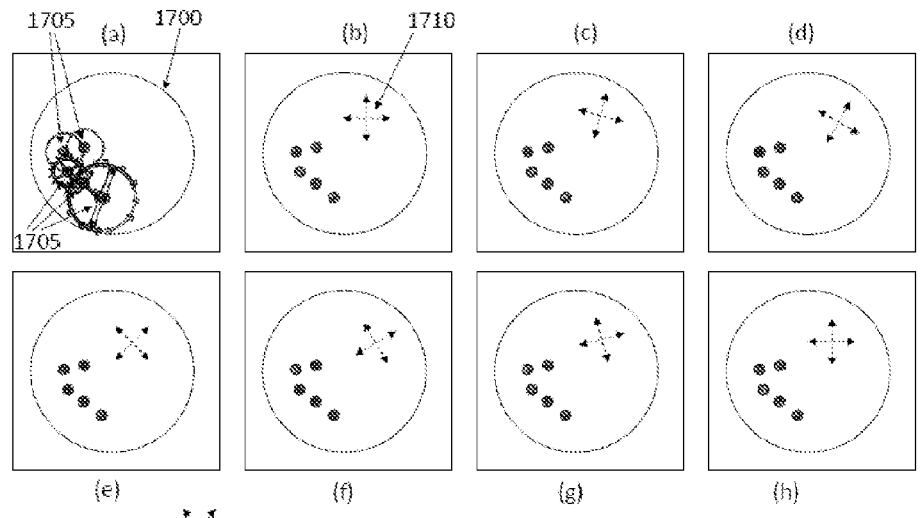
FIG. 17 illustrates views of an exemplary orientation measurement in accordance with aspects of the invention.

FIG. 17 illustrates views of an exemplary orientation measurement in accordance with aspects of the invention. FIG. 17(a) illustrates a schematic view of an exemplary timepiece 1700 (and the viewable jewels 1705 therein). FIGS. 17(b)-17(h) illustrate the exemplary orientation measurement in accordance with aspects of the invention. As should be understood, FIGS. 17(b)-17(h) schematically illustrate watch 1700 with the schematic movement (which is shown in FIG. 17(a)) removed to more clearly illustrate aspects of the present invention. As shown in FIGS. 17(b)-17(h), with this exemplary and non-limiting embodiment, seven measurements of the timepiece 1700 (and the viewable jewels 1705 therein) are taken in 15 degree increments staring at 0 degrees (FIG. 17(b)) and ending at 90 degrees (FIG. 17(h)), for example, using crossed polarizers. The orientation of the crossed polarizers is represented in each of FIGS. 17(b) to 17(h) by reference number 1710. In performing this measurement, the relative orientation of each jewel 1705 can be determined based on the birefringence. While the exemplary embodiment of FIG. 17 illustrates measurements, taken in 15 degree increments, the invention contemplates that in embodiments, other increments (for example, 5 degree increments) may be used to provide a finer or coarser measurement.

Figure 18A:
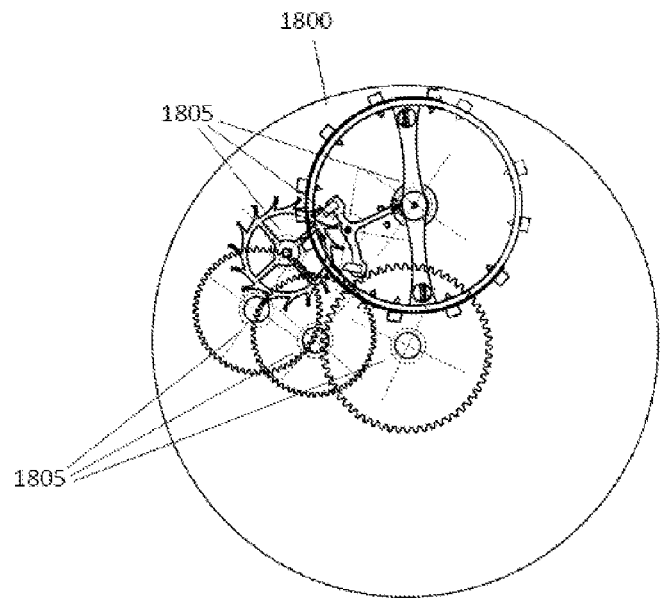
FIGS. 18A and 18B illustrate exemplary results of an orientation measurement in accordance with aspects of the invention.
Figure 18B:
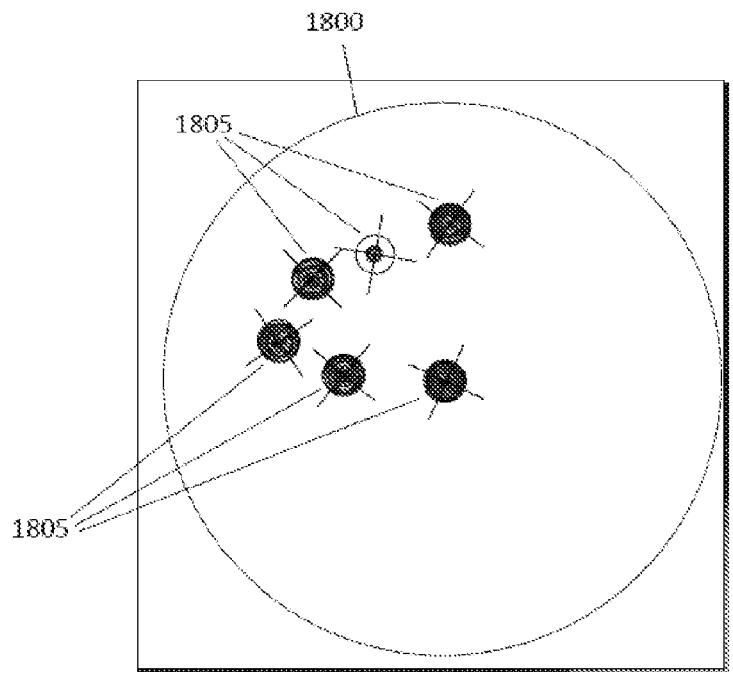

FIGS. 18A and 18B illustrate exemplary results of an orientation measurement in accordance with aspects of the invention. As should be understood, FIGS. 18A and 18B represent schematic illustrations of a watch, and do not illustrate all the components of the watch. Moreover, as can be observed, FIG. 18A illustrates the jewels with additional components of the watch movement, whereas FIG. 18B only illustrates the jewels themselves. As shown in FIGS. 18A and 18B, with this exemplary and non-limiting embodiment, a watch 1800 includes six jewels 1805. In accordance with aspects of the invention, the respective relative orientation of each of the six jewels 1805 are detected and associated (e.g., in a database) with the relative positions of the respective jewels. For example, $\theta_1=35°$, $\theta_2=10°$, $\theta_3=45°$, $\theta_4=35°$, $\theta_5=40°$, $\theta_6=25°$, wherein $\theta$ is the relative orientation, and 1-6 is the jewel number (or relative jewel position). In accordance with aspects of the invention, this association between the orientation and relative locations of the respective jewels creates a map, for example, of which jewel has which orientation, and provides a unique (or substantially unique) identifier or biometric signature for the watch for identification and/or authentication. As should be understood, the invention contemplates that any number of jewels may serve as an identifier or biometric signature, with a larger number of jewels providing a greater level of uniqueness. Additionally, an association between the relative location and both the respective luminescent properties and the respective orientations provide a greater level of identification uniqueness. Moreover, measuring both the luminescent properties and the orientations of the stones does not require much greater time or cost than measuring only one of these properties. In embodiments, there may be 2-10 bits of information per stone.

In further embodiments, the orientation of watch face cover itself, which is usually made of corundum, may serve as an additional identifier of the watch. For example, due to the birefringent properties of the corundum cover, the relative orientation of the cover may be determined, and used as an identifier of the watch. Furthermore, the present invention may utilize a detection of the orientation of the watch face cover to determine if a watch has been tampered with. That is, if a detection of the current watch face cover orientation does not match that of a stored watch face cover orientation for the corresponding watch (e.g., as identified with a serial number), then the present invention indicates that the watch has been tampered with.

Creating Identifier

In accordance with additional aspects of the invention, in embodiments, the measured luminescence properties, relative positions and/or orientations of the respective jewels may be used to create an identifier (e.g., an identification code or map). In embodiments, creating an identifier includes converting the measured information into a digital representation, which can be stored. In embodiments, the identifier is based on one or more of: (i) the position(s) of the stones; (ii) the orientation of the stones; (iii) the luminescence of the stones; and (iv) the value inscribed on one part of the timepiece serving as a first identifier (e.g., the serial number of the case or the movement). In embodiments, the identifier can be a code (e.g., an alphanumeric code) or map, or another type of information related to the measurement (including the raw data, e.g., an image). In embodiments, comparison may be based on the measurement of the stone characteristics (e.g. luminescence or decay time curve, or light reflected from the stone as a function of orientation of the polarizers (for determining the birefringence)), e.g. without determining any relative positions of the stones.

Additionally, in embodiments, the timepiece may be self-authenticating (e.g., authenticatable without comparison to a database of previously identified timepieces). For example, at the manufacturing stage, a manufacturer may determine a code based on the position(s) and one or more of: (i) the orientation; (ii) the luminescence of the stones. This code, for example, in an encrypted format, may then be added on the timepiece as an identification number (e.g., a serial number). Then, upon a subsequent authentication process, the position(s) and one or more of: (i) the orientation; (ii) the luminescence of the stones may be again measured to generate a determined code, which can then be compared to the identification number of the timepiece.

The present invention also contemplates that the stone properties are chosen at the time of manufacture with respect to some pre-determined criteria, associated with other characteristics of the timepiece. For example, a stone with a prescribed lifetime may be chosen for a certain position in a given timepiece model. In embodiments, for example, each gemstone present may have a specific relationship to one or more of the other stones. In further embodiments, the properties of the stones may be chosen to match some other characteristic of the watch (e.g., the serial number). With a non-limiting exemplary embodiment, we can consider an initial code, which is composed with 12 digits, which can be numeric or alphanumeric; for a series of 100 watches. Each of those watches will always have one letter or one number in common (which may be associated with the stone with the prescribed lifetime), and the remaining digits will be based and determined, as mentioned elsewhere in the embodiments and claims. For example, a manufacturer may dictate that for a watch having certain serial numbers (e.g., ending in "2"), the watch must contain a stone having particular properties in position "2." As such, in accordance with aspects of the invention, the watch may be self-authenticating (i.e., without needing to access a database to authenticate). With further embodiments, instead of prescribing particular properties of one or more stones, a watchmaker may prescribe particular relative relationships between the stones. For example, a manufacturer may dictate that the stone in "Position 1" must have a lifetime that is 0.5 ms longer than the stone in "Position 4."

It should be noted that with watch maintenance or repair, the jewels of a movement are not usually adjusted, moved, or replaced. That is, for example, a jewel in "position 1" is not moved to another position. Moreover, during repair the relative orientation of the jewels are not usually adjusted. As such, the present invention is operable to provide identification and/or authentication of a watch even if the watch has been maintained or repaired. In the event that jewels are replaced, or the entire movement is replaced, the watch would need to be re-recorded (e.g., recertified as authentic). Upon re-recording, for example, in accordance with aspects of the invention, the watch may be analyzed again to determine a new identifier (e.g., map or identifying code) for the watch. This new identifier will replace the old identifier, and may be stored in a database in association with the watch alphanumeric identifier (e.g., serial number).

The present invention provides a robust solution, as the jewels' properties (e.g., luminescence, orientation, and position) will not change substantially with time. Additionally, the present invention utilizes timepiece components that are naturally present, thus requiring no change of assembly process. The present invention utilizes properties that are easily measured. In embodiments, the present invention utilizes several bits of information per stone (or jewel). Additionally, in accordance with aspects of the invention, the stones can be configured with more bits per stone. As the jewels' properties (e.g., luminescence, orientation, and position) can be measured, for example, at manufacture, the present invention provides a degree of tamper evidence. In accordance with aspects of the invention, the position, orientation, luminescence of the stones can be deliberately specified at the manufacturing to create a specific code, or taken as such from the manufacturer. For example, the orientations of one or more stones may be imposed by a manufacturer to create, for example, a predetermined identifying code.

EXAMPLE

With a non-limiting exemplary embodiment, a watch manufacturer or a merchant, for example, may perform an analysis of a watch to determine an identification code based on the position(s) of the stones and one or more of: (i) the orientation; (ii) the luminescence of the stones. Subsequently, by performing an analysis of the watch to determine a created identification code based on the position(s) of the stones and one or more of: (i) the orientation; (ii) the luminescence of the stones, and comparing the created identification code to one or more stored identification codes, a watch owner, a manufacturer, customs, and/or a repair shop, amongst others, for example, can have the watch authenticated.

As should be understood, in embodiments, the initial analysis of the watch (to create the identification code) may be performed downstream from the original manufacturing. For example, a watch owner may have their used watch analyzed to determine an identification code, which may then be sent to the watchmaker for future authentication and/or identification.

System Environment

As will be appreciated by one skilled in the art, the present invention may be embodied as a timepiece, a system, a method or a computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electro-magnetic, infrared, or semiconductor system, apparatus, device, or propagation medium. More specific examples (a non-exhaustive list) of the computer-readable medium would include the following:

an electrical connection having one or more wires,
a portable computer diskette,
a hard disk,
a random access memory (RAM),
a read-only memory (ROM),
an erasable programmable read-only memory (EPROM or Flash memory),
an optical fiber,
a portable compact disc read-only memory (CDROM),
an optical storage device,
a transmission media such as those supporting the Internet or an intranet,
a magnetic storage device
a usb key,
a certificate,
a perforated card, and/or
a mobile phone.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider). Additionally, in embodiments, the present invention may be embodied in a field programmable gate array (FPGA).

Figure 19:
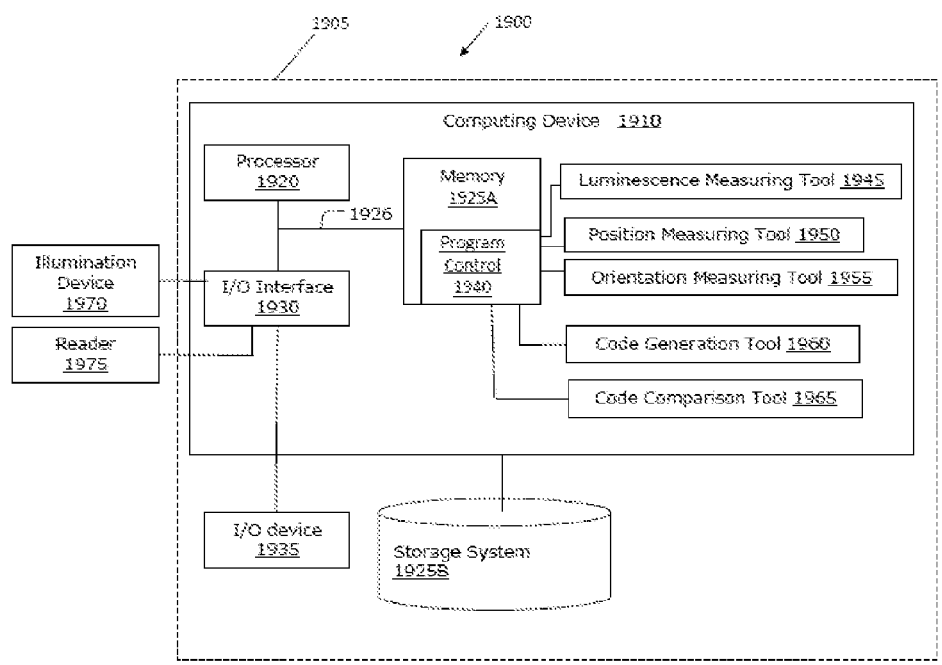
FIG. 19 shows an illustrative environment 1900 for managing the processes in accordance with the invention.

FIG. 19 shows an illustrative environment 1900 for managing the processes in accordance with the invention. To this extent, the environment 1900 includes a server or other computing system 1905 that can perform the processes described herein. In particular, the server 1905 includes a computing device 1910. The computing device 1910 can be resident on a network infrastructure or computing device of a third party service provider (any of which is generally represented in FIG. 1900).

In embodiments, the computing device 1910 includes a luminescence measuring tool 1945, a position measuring tool 1950, an orientation measuring tool 1955, a code generation tool 1960, and a code comparison tool 1965, which are operable to measure one or more detected luminescent properties, measure one or more detected relative positions, measure one or more detected relative orientations, generate an identification code based on relative position, the luminescent properties, the relative orientations, and/or the serial number, and compare measured properties or measured codes with stored properties or stored codes e.g., the processes described herein. The luminescence measuring tool 1945, the position measuring tool 1950, the orientation measuring tool 1955, the code generation tool 1960, and the code comparison tool 1965 can be implemented as one or more program code in the program control 1940 stored in memory 1925A as separate or combined modules.

The computing device 1910 also includes a processor 1920, memory 1925A, an I/O interface 1930, and a bus 1926. The memory 1925A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 1910 is in communication with the external I/O device/resource 1935 and the storage system 1925B. For example, the I/O device 1935 can comprise any device that enables an individual to interact with the computing device 1910 or any device that enables the computing device 1910 to communicate with one or more other computing devices using any type of communications link. The external I/O device/resource 1935 may be for example, a handheld device, PDA, handset, keyboard, smartphone, etc. Additionally, in accordance with aspects of the invention, the environment 1900 includes an illumination device 1970 for providing illumination, and one or more readers 1975 for measuring luminescent properties, relative position, and/or relative orientation of the jewels.

In general, the processor 1920 executes computer program code (e.g., program control 1940), which can be stored in the memory 1925A and/or storage system 1925B. Moreover, in accordance with aspects of the invention, the program control 1940 having program code controls the luminescence measuring tool 1945, the position measuring tool 1950, the orientation measuring tool 1955, the code generation tool 1960, and the code comparison tool 1960. While executing the computer program code, the processor 1920 can read and/or write data to/from memory 1925A, storage system 1925B, and/or I/O interface 1930. The program code executes the processes of the invention. The bus 1926 provides a communications link between each of the components in the computing device 1910.

The computing device 1910 can comprise any general purpose computing article of manufacture capable of executing computer program code installed thereon (e.g., a personal computer, server, etc.). However, it is understood that the computing device 1910 is only representative of various possible equivalent-computing devices that may perform the processes described herein. To this extent, in embodiments, the functionality provided by the computing device 1910 can be implemented by a computing article of manufacture that includes any combination of general and/or specific purpose hardware and/or computer program code. In each embodiment, the program code and hardware can be created using standard programming and engineering techniques, respectively.

Similarly, the computing infrastructure 1905 is only illustrative of various types of computer infrastructures for implementing the invention. For example, in embodiments, the server 1905 comprises two or more computing devices (e.g., a server cluster) that communicate over any type of communications link, such as a network, a shared memory, or the like, to perform the process described herein. Further, while performing the processes described herein, one or more computing devices on the server 1905 can communicate with one or more other computing devices external to the server 1905 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Flow Diagrams

Figure 20:
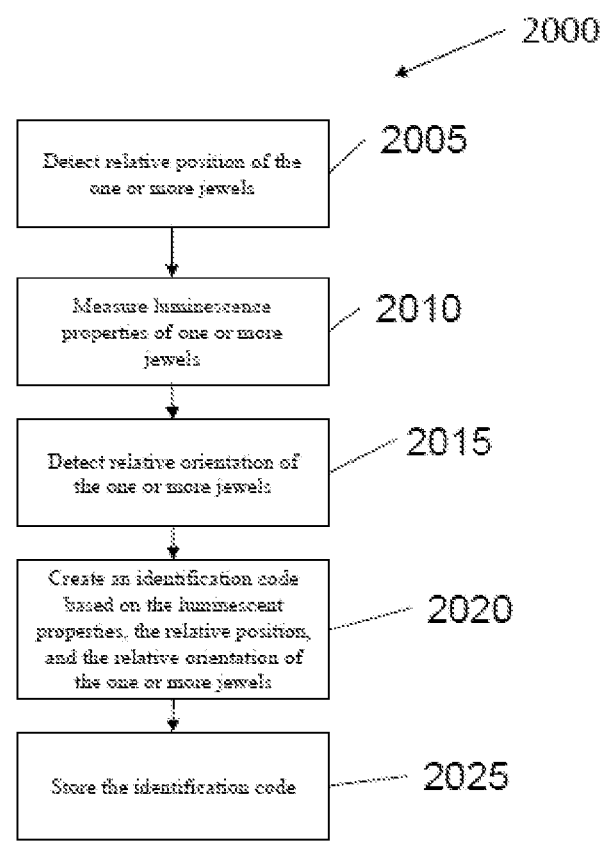
FIGS. 20 and 21 show exemplary flows for performing aspects of the present invention.
Figure 21:
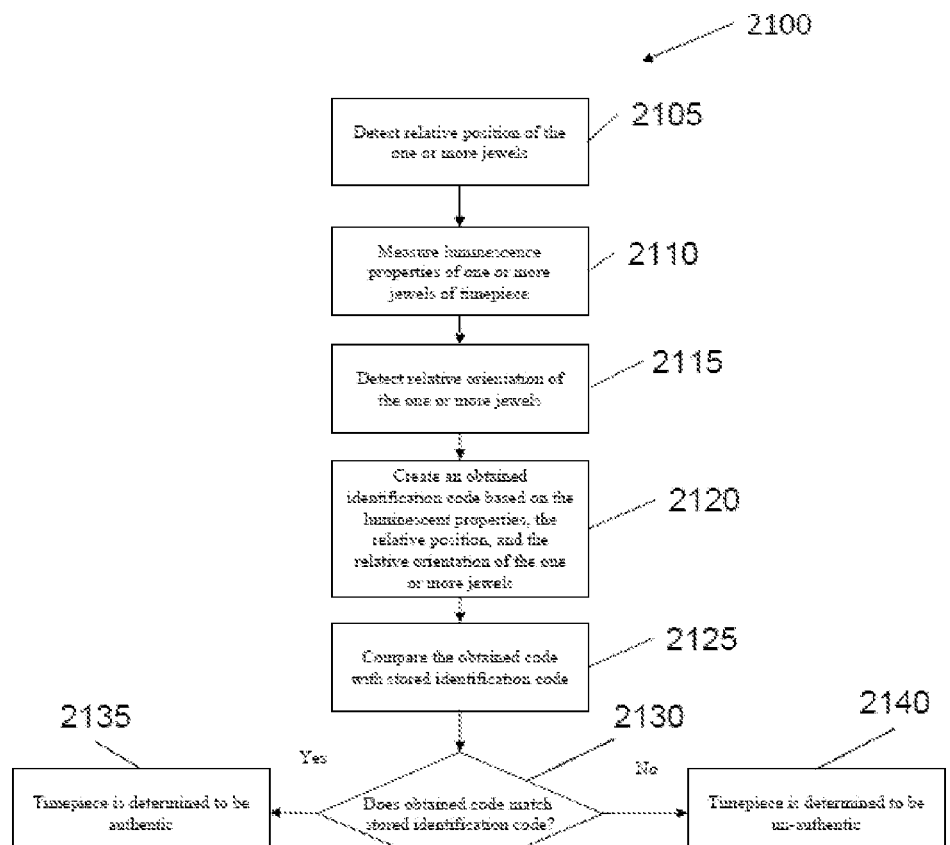

FIGS. 20 and 21 show exemplary flows for performing aspects of the present invention. The steps of FIGS. 20 and 21 may be implemented in the environment of FIG. 19, for example. The flow diagrams may equally represent a high-level block diagrams of the invention. The flowcharts and/or block diagrams in FIGS. 20 and 21 illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of each flowchart, and combinations of the flowchart illustrations can be implemented by special purpose hardware-based systems that perform the specified functions or acts, or combinations of special purpose hardware and computer instructions and/or software, as described above. Moreover, the steps of the flow diagrams may be implemented and executed from either a server, in a client server relationship, or they may run on a user workstation with operative information conveyed to the user workstation. In an embodiment, the software elements include firmware, resident software, microcode, etc.

Furthermore, the invention can take the form of a computer program product accessible from a computer-usable or computer-readable medium providing program code for use by or in connection with a computer or any instruction execution system. The software and/or computer program product can be implemented in the environment of FIG. 19. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disc-read/write (CD-R/W) and DVD.

FIG. 20 illustrates an exemplary flow 2000 for creating and storing an identification code for a timepiece. At step 2005, the position measuring tool detects the relative position of the one or more jewels. As shown in FIG. 20, at step 2010, the luminescence measuring tool measures luminescence properties of one or more jewels, for example, at one or more intervals. At step 2015, the orientation measuring tool detects the relative orientation of the one or more jewels. At step 2020, the code generation tool creates an identification code based on the relative position, the luminescent properties, and/or the relative orientation of the one or more jewels. In embodiments, the code generation tool may additionally utilize a serial number of the timepiece in creating the identification code. At step 2025, the code generation tool stores the identification code in a storage system, e.g., a database.

FIG. 21 illustrates an exemplary flow 2100 for authentication and/or identification of a time piece. As shown in FIG. 21, at step 2105, the position measuring tool detects the relative position of the one or more jewels. At step 2110, the luminescence measuring tool measures luminescence properties of one or more jewels, for example, at one or more intervals. At step 2115, the orientation measuring tool detects the relative orientation of the one or more jewels. At step 2120, the code creation tool creates an obtained identification code based on the luminescent properties, the relative position, and the relative orientation of the one or more jewels. At step 2125, the code comparison tool compares the obtained code with stored identification codes. At step 2130, the code comparison tool determines whether the obtained code matches a stored identification code. If, at step 2130, the code comparison tool determines that the obtained code matches a stored identification code, at step 2135, the timepiece is determined to be authentic. If, at step 2130, the code comparison tool determines that the obtained code match does not match a stored identification code, at step 2140, the timepiece is determined to be un-authentic.

While the invention has been described with reference to specific embodiments, those skilled in the art will understand that various changes may be made and equivalents may be substituted for elements thereof without departing from the true spirit and scope of the invention. In addition, modifications may be made without departing from the essential teachings of the invention.

What is claimed is:

1. A method for authentication and/or identification of a timepiece having at least one gemstone being part of a timepiece movement of the timepiece, the method comprising:

measuring at least one of luminescent properties of the at least one gemstone and birefringence properties of the at least one gemstone;

detecting a relative position of the at least one gemstone in the timepiece;

creating an identifier for the timepiece in dependence upon the at least one of the measured luminescent properties and the measured birefringence properties of the at least one gemstone, and the respective relative position of the at least one gemstone; and comparing the created identifier with one or more stored identifiers to determine whether the timepiece is authentic or a counterfeit.

2. A system for determining an identifier from a timepiece having at least one gemstone being part of a timepiece movement of the timepiece, the system comprising:

at least one reader configured to determine one or more characteristics and detect a relative position of the at least one gemstone in the timepiece;

a processor for creating the identifier for the timepiece in dependence upon at least one of the one or more characteristics of the at least one gemstone and the respective relative position of the at least one gemstone; and a storage system configured for storing the identifier.

* * * * *